US012785589B2

(12) United States Patent
Palaniswamy et al.

(10) Patent No.: US 12,785,589 B2
(45) Date of Patent: Nov. 3, 2026

(54) ARTIFICIAL MUSCLES, ARTIFICIAL MUSCLE ASSEMBLIES, AND METHODS OF USING SAME

(71) Applicant: Toyota Motor Engineering & Manufacturing North America, Inc., Plano, TX (US)

(72) Inventors: Maduran Palaniswamy, Ann Arbor, MI (US); Erin Rutledge, Tipton, MI (US); Michael P. Rowe, Pinckney, MI (US)

(73) Assignees: TOYOTA MOTOR ENGINEERING & MANUFACTURING NORTH AMERICA, INC., Plano, TX (US); TOYOTA JIDOSHA KABUSHIKI KAISHA, Toyota (JP)

( * ) Notice: Subject to any disclaimer, the term of this patent is extended or adjusted under 35 U.S.C. 154(b) by 798 days.

(21) Appl. No.: 18/116,419

(22) Filed: Mar. 2, 2023

(65) Prior Publication Data

US 2024/0293220 A1 Sep. 5, 2024

(51) Int. Cl.
*H02N 1/00* (2006.01)
*A61F 2/70* (2006.01)
(Continued)

(52) U.S. Cl.
CPC ............... *H02N 1/006* (2013.01); *A61F 2/70* (2013.01); *B25J 9/1075* (2013.01); *A61F 2002/5066* (2013.01); *B25J 9/142* (2013.01)

(58) Field of Classification Search
CPC . B25J 9/1075; B25J 9/142; A61F 2/70; A61F 2002/5066; H02N 1/006
See application file for complete search history.

(56) References Cited

U.S. PATENT DOCUMENTS 11,372,481 B2 * 6/2022 Leroy ..................... G06F 3/014
11,486,421 B2 * 11/2022 Keplinger ............... F15B 15/10
(Continued)

FOREIGN PATENT DOCUMENTS

CN 113078407 A 7/2021
KR 20170104826 A 9/2017
(Continued)

*Primary Examiner* — Dustin T Nguyen
(74) *Attorney, Agent, or Firm* — Dinsmore & Shohl LLP

(57) ABSTRACT

An artificial muscle including a housing, an electrode pair positioned in an electrode region of the housing, the electrode pair including a first electrode and a second electrode, the first electrode and the second electrode each including a pair of tapered tab portions and a bridge portion, the tapered tab portions each having a first end proximate to the expandable fluid region and an opposite second end proximate the electrode region, each of the second ends tapering in a direction opposite the expandable fluid region, the pair of tapered tab portions extending parallel to one another to define a gap portion between the pair of tapered tab portions, the bridge portion interconnecting the pair of tapered tab portions, and a dielectric fluid housed within the housing, wherein the electrode pair is actuatable between a non-actuated state and an actuated state such that actuation from the non-actuated state to the actuated state directs the dielectric fluid into an expandable fluid region of the housing.

14 Claims, 6 Drawing Sheets

(51) Int. Cl.
*B25J 9/10* (2006.01)
*B25J 9/14* (2006.01)
*A61F 2/50* (2006.01)

(56) References Cited

U.S. PATENT DOCUMENTS

| | | | | |
|---|---|---|---|---|
| 11,491,647 | B2 * | 11/2022 | Rowe | H02N 1/006 |
| 11,949,349 | B2 * | 4/2024 | Rowe | F15B 21/065 |
| 12,023,806 | B2 * | 7/2024 | Zou | B25J 9/12 |
| 12,194,894 | B2 * | 1/2025 | Acome | A47C 7/462 |
| 12,199,527 | B2 * | 1/2025 | Rowe | B25J 9/1075 |
| 12,199,528 | B2 * | 1/2025 | Rutledge | H02N 1/006 |
| 2020/0393452 | A1 | 12/2020 | Pamula et al. | |
| 2022/0176551 | A1 | 6/2022 | Rowe et al. | |
| 2022/0232903 | A1 | 7/2022 | Rutledge et al. | |
| 2023/0091400 | A1 * | 3/2023 | Acome | H02N 1/006<br>294/119.3 |

FOREIGN PATENT DOCUMENTS

| | | | |
|---|---|---|---|
| WO | 2019173227 | A1 | 9/2019 |
| WO | 2021030742 | A1 | 2/2021 |

* cited by examiner

ARTIFICIAL MUSCLES, ARTIFICIAL MUSCLE ASSEMBLIES, AND METHODS OF USING SAME

TECHNICAL FIELD

The present specification generally relates to apparatus and methods for focused inflation on at least one surface of a device, and, more specifically, apparatus and methods for utilizing a tapered electrode pair to direct a fluid to inflate the device.

BACKGROUND

Current robotic technologies rely on rigid components, such as servomotors to perform tasks, often in a structured environment. This rigidity presents limitations in many robotic applications, caused, at least in part, by the weight-to-power ratio of servomotors and other rigid robotics devices. The field of soft robotics improves on these limitations by using artificial muscles and other soft actuators. Artificial muscles attempt to mimic the versatility, performance, and reliability of a biological muscle. Some artificial muscles rely on fluidic actuators, but fluidic actuators require a supply of pressurized gas or liquid, and fluid transport must occur through systems of channels and tubes, limiting the speed and efficiency of the artificial muscles. Other artificial muscles use thermally activated polymer fibers, but these are difficult to control and operate at low efficiencies.

Accordingly, a need exists for improved artificial muscles with increased actuator power per unit volume.

SUMMARY

In one embodiment, an artificial muscle includes: a housing including an electrode region and an expandable fluid region; an electrode pair positioned in the electrode region of the housing, the electrode pair including a first electrode and a second electrode, the first electrode and the second electrode each including a pair of tapered tab portions and a bridge portion interconnecting the pair of tapered tab portions, the tapered tab portions each having a first end proximate to the expandable fluid region and an opposite second end proximate the electrode region, each of the second ends tapering in a direction opposite the expandable fluid region, the pair of tapered tab portions extending parallel to one another to define a gap portion between the pair of tapered tab portions; and a dielectric fluid housed within the housing, wherein the electrode pair is actuatable between a non-actuated state and an actuated state such that actuation from the non-actuated state to the actuated state directs the dielectric fluid into the expandable fluid region.

In another embodiment an electrode includes a tapered tab portion and a terminal. The tapered tab portion has a first end and an opposite second end, the first end proximate to an expandable fluid region and the second end proximate to an electrode region. The second end tapers in a direction opposite the expandable fluid region. The terminal extends from the second end of the tapered tab portion.

In yet another embodiment, a method for actuating an artificial muscle assembly includes: generating a voltage using a power supply electrically coupled to an electrode pair of an artificial muscle, the artificial muscle including a housing with an electrode region and an expandable fluid region, wherein: the electrode pair is positioned in the electrode region of the housing; the electrode pair including a first electrode and a second electrode, the first electrode and the second electrode each comprise a pair of tapered tab portions and a bridge portion interconnecting the pair of tapered tab portions, the tapered tab portions each having a first end proximate to the expandable fluid region and an opposite second end proximate the electrode region, each of the second ends tapering in a direction opposite the expandable fluid region, the pair of tapered tab portions extending parallel to one another to define a gap portion between the pair of tapered tab portions, and a dielectric fluid is housed within the housing; and applying the voltage to the electrode pair of the artificial muscle, thereby actuating the electrode pair from a non-actuated state and an actuated state such that the dielectric fluid is directed into the expandable fluid region of the housing and expands the expandable fluid region.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
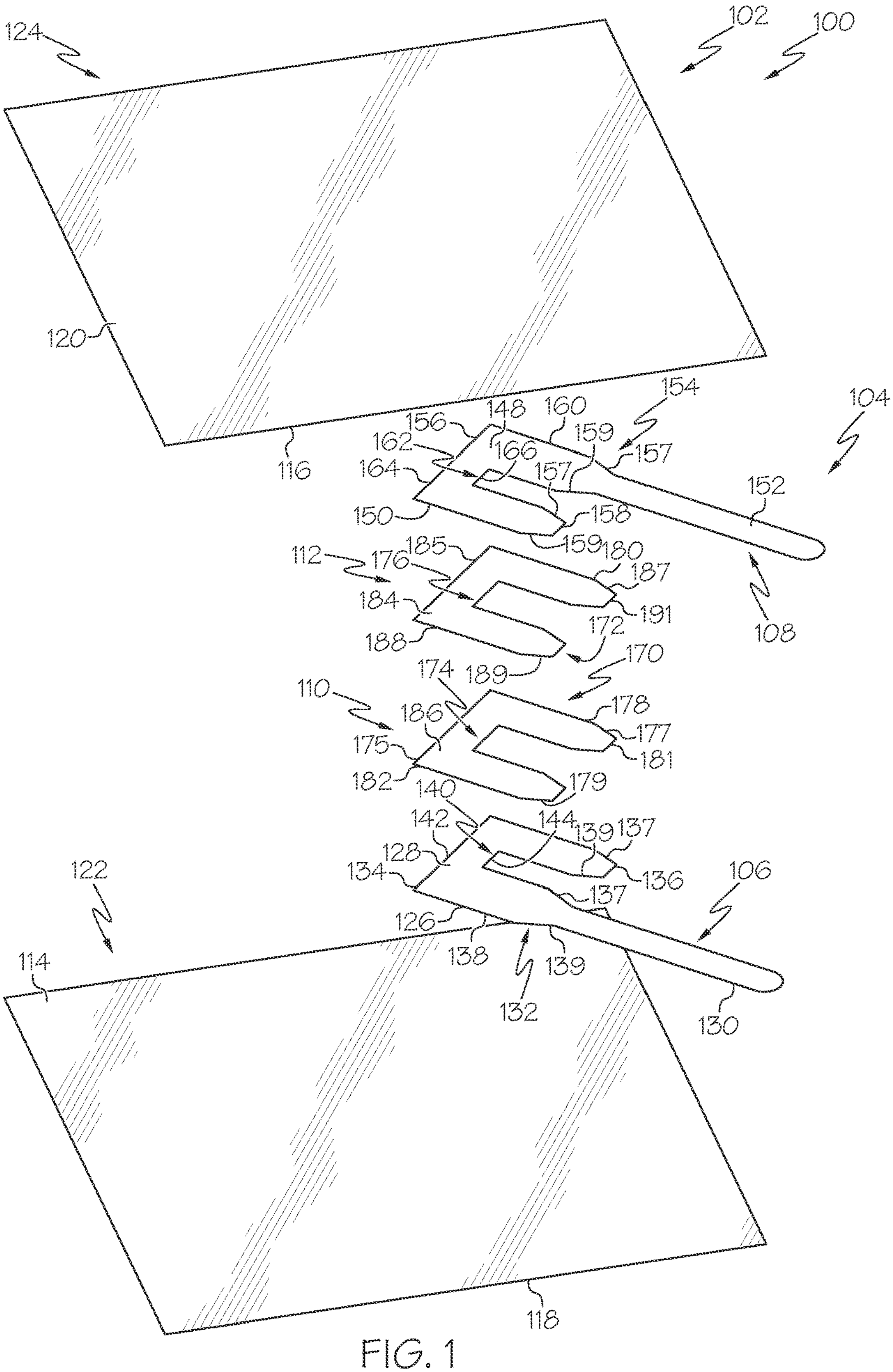
FIG. 1 schematically depicts an exploded view of an artificial muscle, according to one or more embodiments shown and described herein.

Embodiments described herein are directed to artificial muscles and artificial muscle assemblies that include a plurality of artificial muscles. The artificial muscles described herein are actuatable to selectively raise and lower a region of the artificial muscles to provide a selective, on demand inflated expandable fluid region. The artificial muscles include a housing and an electrode pair. A dielectric fluid is housed within the housing, and the housing includes an electrode region and an expandable fluid region, where the electrode pair is positioned in the electrode region. The electrode pair includes a first electrode and a second electrode. The electrode pair is actuatable between a non-actuated state and an actuated state such that actuation from the non-actuated state to the actuated state directs the dielectric fluid into the expandable fluid region. This expands the expandable fluid region, raising a portion of the artificial muscle on demand. Further, the first electrode and the second electrode each includes a pair of tapered tab portions and a bridge portion interconnecting the tapered tab portions. The tapered tab portion and bridge portion design of the electrode pair facilitates a zippering actuation motion to increase the force per unit volume achievable by actuation of the artificial muscle. Various embodiments of the artificial muscle and the operation of the artificial muscle are described in more detail herein. Whenever possible, the same reference numerals will be used throughout the drawings to refer to the same or like parts.

Referring now to FIG. 1, an artificial muscle 100 is shown. The artificial muscle 100 includes a housing 102, an electrode pair 104, including a first electrode 106 and a second electrode 108, coupled or otherwise fixed to opposite surfaces of the housing 102, a first electrical insulator layer 110 fixed to the first electrode 106, and a second electrical insulator layer 112 fixed to the second electrode 108. In some embodiments, the housing 102 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 102 are heat sealable. In embodiments, the housing 102 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

Throughout the ensuing description, reference may be made to the housing 102 including the first film layer 122 and the second film layer 124, as opposed to the one-piece housing. It should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene (BOPP).

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In some embodiments, the first electrode 106 and the second electrode 108 may be flexible. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 100 is negatively charged.

Figure 7:
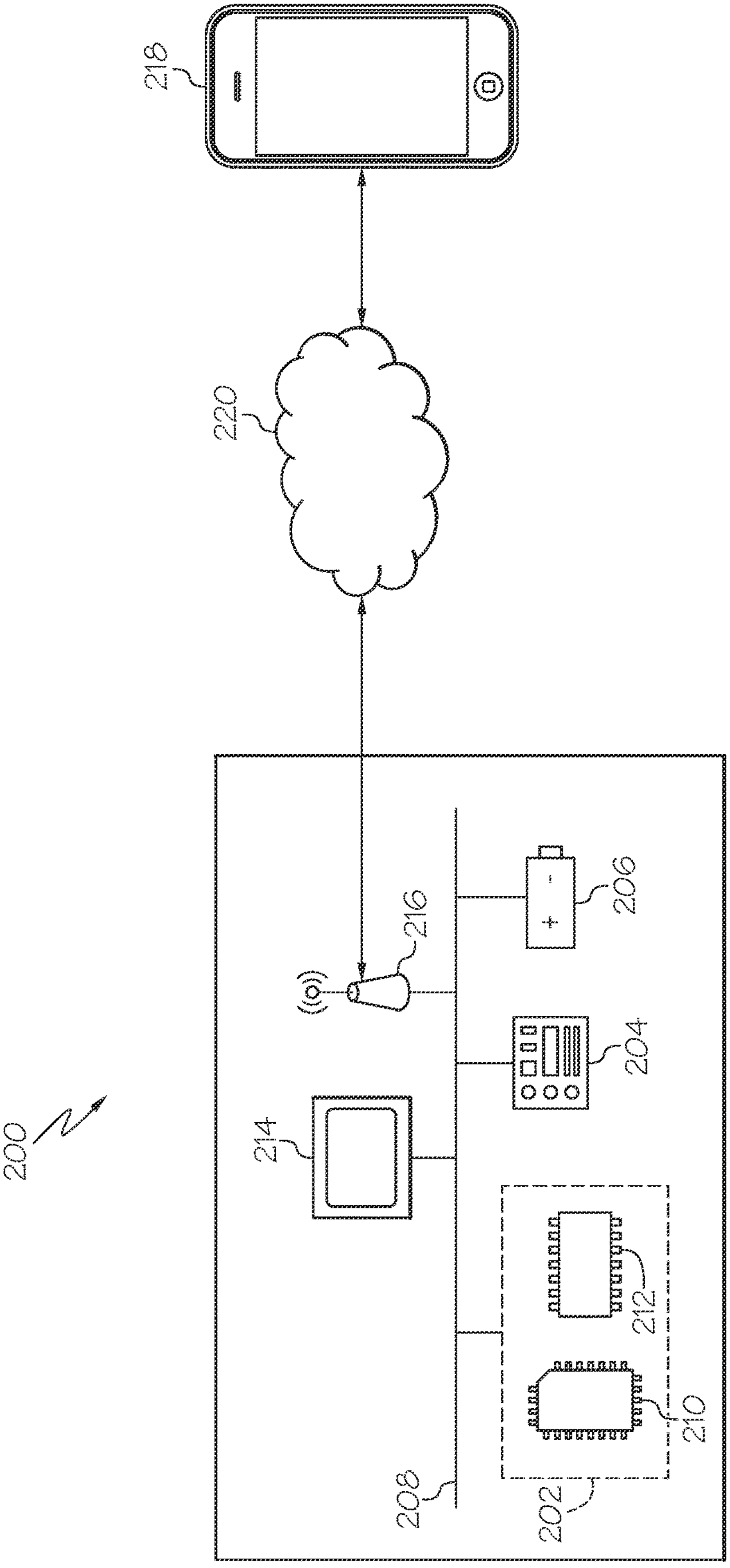
FIG. 7 schematically depicts an actuation system for operating the artificial muscle of FIG. 1, according to one or more embodiments shown and described herein.

Referring still to FIG. 1, the first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the first terminal 130 is coupled, either directly or in series, to a power supply and a controller of an actuation system 200, as shown in FIG. 7. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 200 to actuate the second electrode 108.

Figure 2:
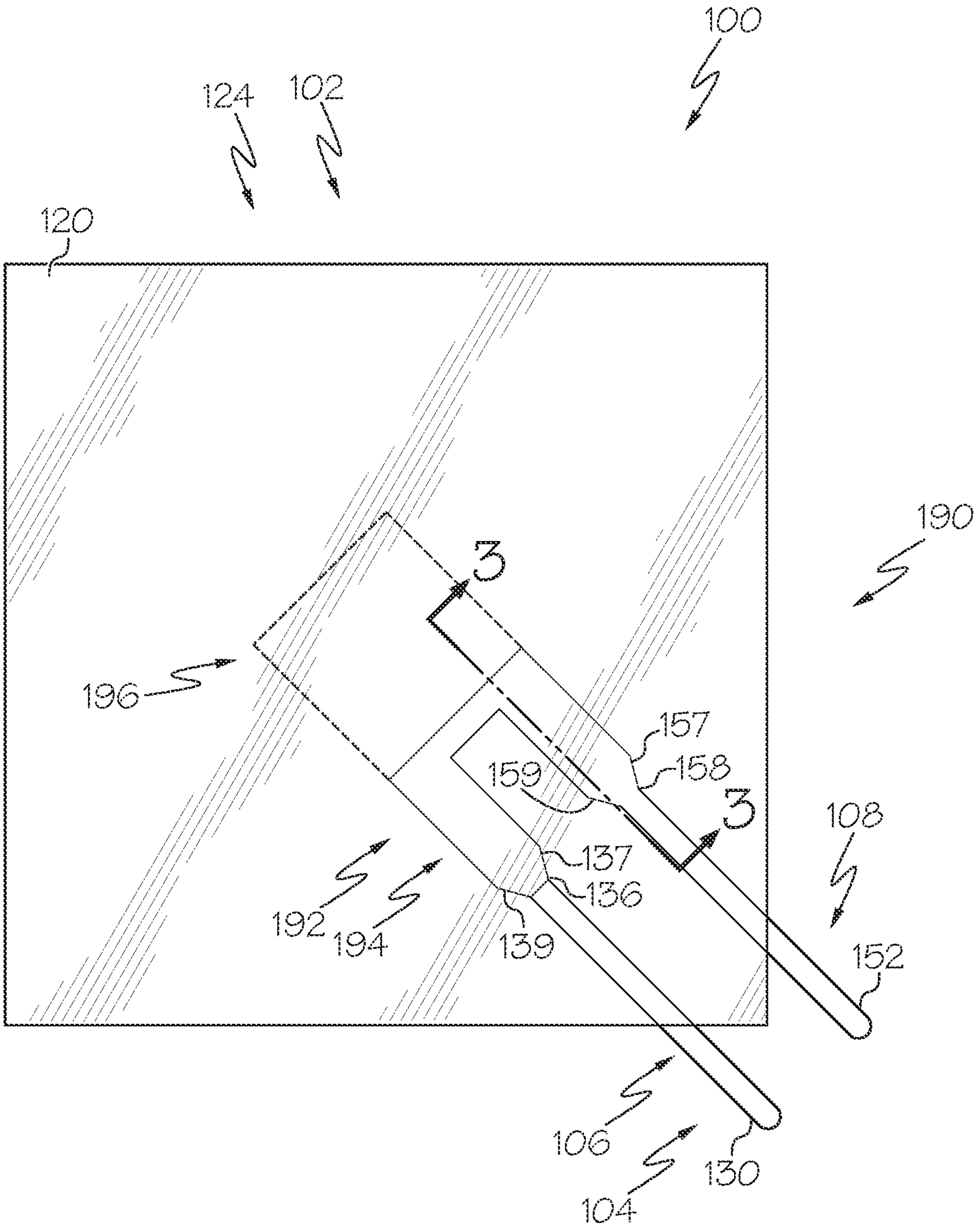
FIG. 2 schematically depicts a top view of the artificial muscle of FIG. 1, according to one or more embodiments shown and described herein.

In embodiments, the first electrode 106 includes a pair of tapered tab portions 132 and a bridge portion 140. The bridge portion 140 is positioned between the tapered tab portions 132 and interconnects the tapered tab portions 132. Although only a pair of tapered tab portions 132 are illustrated extending substantially parallel to one another with a single bridge portion 140 extending therebetween, it should be appreciated that the first electrode 106 may include more than two tapered tab portions 132 and more than one bridge portion 140. For example, the first electrode 106 may include three tapered tab portions 132 and a pair of bridge portions 140 with each bridge portion 140 extending between a pair of adjacent tapered tab portions 132. Each tapered tab portion 132 has a first end 134 and an opposite second end 136 proximate the first terminal 130 of the first electrode 106 and defining a portion of an outer perimeter 138 of the first electrode 106. Each tapered tab portion 132 includes two tapered walls 137, 139 where the distance between the tapered walls 137, 139 decreases from a point between the first end 134 and the second end 136 in a direction towards the second end 136. As shown in FIG. 2, the first terminal 130 extends from the second end 136 of one of the tapered tab portions 132 at a central point between the two tapered walls 137, 139 and is integrally formed therewith. Each bridge portion 140 has a first end 142 and an opposite second end 144 defining another portion of the outer perimeter 138 of the first electrode 106. In some embodiments, junctions, joining portions, edges, and the like formed along the outer perimeter 138 of the tapered tab portions 132 are slightly rounded or chamfered.

Like the first electrode 106, in embodiments, the second electrode 108 includes a pair of tapered tab portions 154 and a bridge portion 162. The bridge portion 162 is positioned between the tapered tab portions 154 and interconnects the tapered tab portions 154. Although only a pair of tapered tab portions 154 are illustrated extending parallel to one another with a single bridge portion 162 extending therebetween, it should be appreciated that the second electrode 108 may include more than two tapered tab portions 154 and more than one bridge portion 162. For example, the second electrode 108 may include three tapered tab portions 154 and a pair of bridge portions 162 with each bridge portion 162 extending between a pair of adjacent tapered tab portions 154. Each tapered tab portion 154 has a first end 156 and an opposite second end 158 proximate the second terminal 152 of the second electrode 108 and defining a portion of an outer perimeter 160 of the second electrode 108. Each tapered tab portion 154 includes two tapered walls 157, 159 where the distance between the tapered walls 157, 159 decreases from a point between the first end 156 and the second end 158 in a direction towards the second end 158. As shown in FIG. 1, the second terminal 152 extends from the second end 158 of one of the tapered tab portions 154 at a central point between the two tapered walls 157, 159 and is integrally formed therewith. Each bridge portion 162 has a first end 164 and an opposite second end 166 defining another portion of the outer perimeter 160 of the second electrode 108. In some embodiments, junctions, joining portions, edges, and the like formed along the outside perimeter 160 of the tapered tab portion 154 are slightly rounded or chamfered.

Referring still to FIG. 1, the first electrical insulator layer 110 and the second electrical insulator layer 112 have a geometry generally corresponding to the first electrode 106 and the second electrode 108, respectively. Thus, the first electrical insulator layer 110 and the second electrical insulator layer 112 each have tapered tab portions 170, 172, and bridge portions 174, 176 corresponding to like portions on the first electrode 106 and the second electrode 108. Each tapered tab portion 170, 172 includes two tapered walls 177, 179, 187, 189 where the distance between the tapered walls 177, 179, 187, 189 decreases from a point between a first end 175, 185 and an opposite second end 181, 191 in a direction towards the second end 181, 191. Further, the first electrical insulator layer 110 and the second electrical insulator layer 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first electrical insulator layer 110 and the second electrical insulator layer 112 generally include the same structure and composition. As such, in some embodiments, the first electrical insulator layer 110 and the second electrical insulator layer 112 each includes a sealable surface 182, 184 and an opposite non-sealable surface 186, 188, respectively. Thus, in some embodiments, the first electrical insulator layer 110 and the second electrical insulator layer 112 are each a polymer tape adhered to the inner surface 128 of the first electrode 106 and the inner surface 150 of the second electrode 108, respectively. In embodiments, the first electrical insulator layer 110 and the second electrical insulator layer 112 each comprises poly(vinylidene fluoride)-co-bexafluoropropylene (PVDF-HFP) film. Each of the first electrical insulator layer 110 and the second electrical insulator layer 112 may have a thickness of between 1 micron and 3 microns. In embodiments, each of the first electrical insulator layer 110 and the second electrical insulator layer 112 may have a thickness of 2 microns. The first electrical insulator layer 110 and the second electrical insulator layer 112 may be attached to the first electrode 106 and the second electrode 108, respectively, by being vacuum heat sealed.

Referring now to FIG. 2, the artificial muscle 100 is shown in its assembled form with the first terminal 130 of the first electrode 106 and the second terminal 152 of the second electrode 108 extending past an outer perimeter of the housing 102, i.e., the first film layer 122 and the second film layer 124. As shown in FIG. 2, the second electrode 108 is stacked on top of the first electrode 106 and, therefore, only the first terminal 130 of the first electrode 106 is shown and the first film layer 122, the first electrical insulator layer 110, and the second electrical insulator layer 112 are not shown.

With reference to FIGS. 2-5, in an assembled form, the first electrode 106, the second electrode 108, the first electrical insulator layer 110, and the second electrical insulator layer 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 at least partially surrounding the first electrode 106 and the second electrode 108. The first film layer 122 and the second film layer 124 may be sealed in any suitable manner, such as using an adhesive, heat sealing, or the like.

An unsealed portion 192 is provided adjacent the sealed portion 190 at which the first film layer 122 is prevented from sealing to the second film layer 124. The unsealed portion 192 of the housing 102 includes an electrode region 194, in which the electrode pair 104 is provided, and an expandable fluid region 196, which is surrounded by the electrode region 194 and the sealed portion 190. Although not shown, the housing 102 may be cut to conform to the geometry of the electrode pair 104 and reduce the size of the artificial muscle 100, namely, the size of the sealed portion 190.

Figure 4:
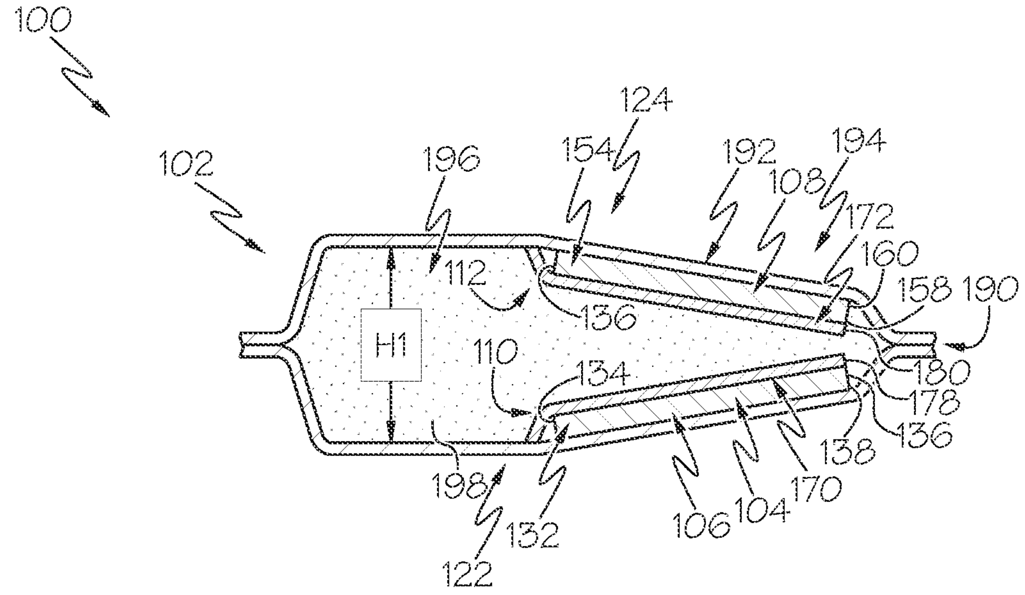
FIG. 4 schematically depicts an assembled, cross-sectional view of the artificial muscle of FIG. 1 taken along line 3-3 in FIG. 2 in a non-actuated state, according to one or more embodiments shown and described herein.
Figure 5:
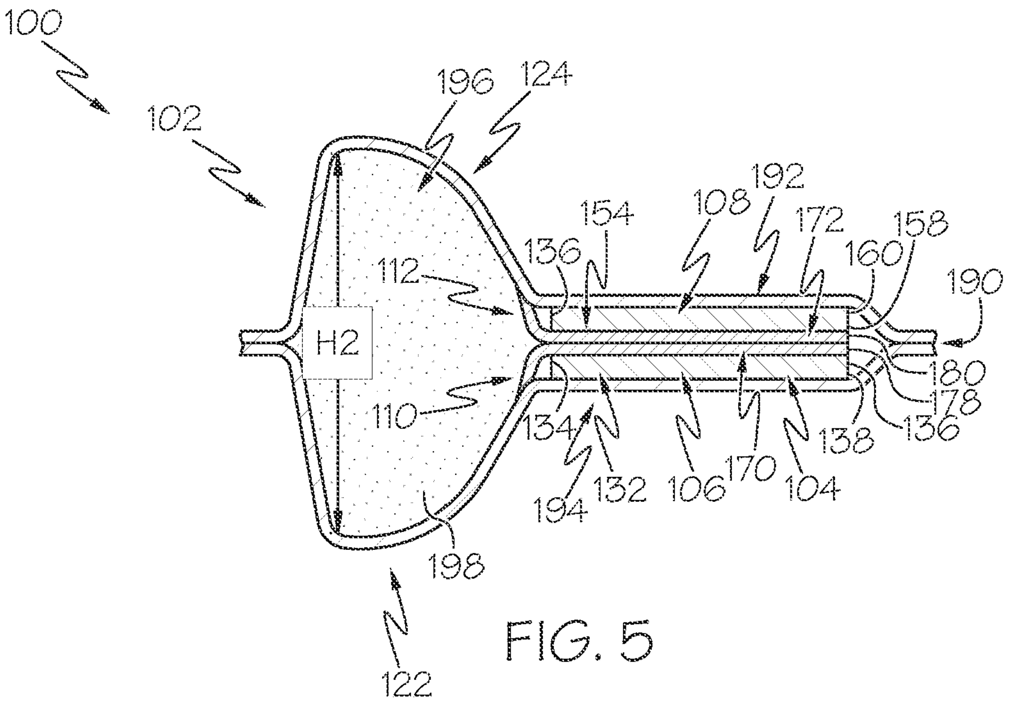
FIG. 5 schematically depicts an assembled, cross-sectional view of the artificial muscle of FIG. 1 taken along line 3-3 in FIG. 2 in an actuated state, according to one or more embodiments shown and described herein.

As shown in FIGS. 4 and 5, a dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 100 using a needle or other suitable injection device.

Referring again to FIG. 3, in embodiments, the first film layer 122 and the second film layer 124 each include more than one layer. For example, the first film layer 122 includes a first inner subfilm layer **122*a* defining the first inner surface 114 and a first outer subfilm layer 122*b* defining the first outer surface 118, and the second film layer 124 includes a second inner subfilm layer 124*a* defining the second inner surface 116 and a second outer subfilm layer 124*b* defining the second outer surface 120. In embodiments, one or more additional layers may be provided between the first inner subfilm layer 122*a* and the first outer subfilm layer 122*b*. Similarly, in embodiments, one or more additional layers may be provided between the second inner subfilm layer 124*a* and the second outer subfilm layer 124*b***.

Figure 3:
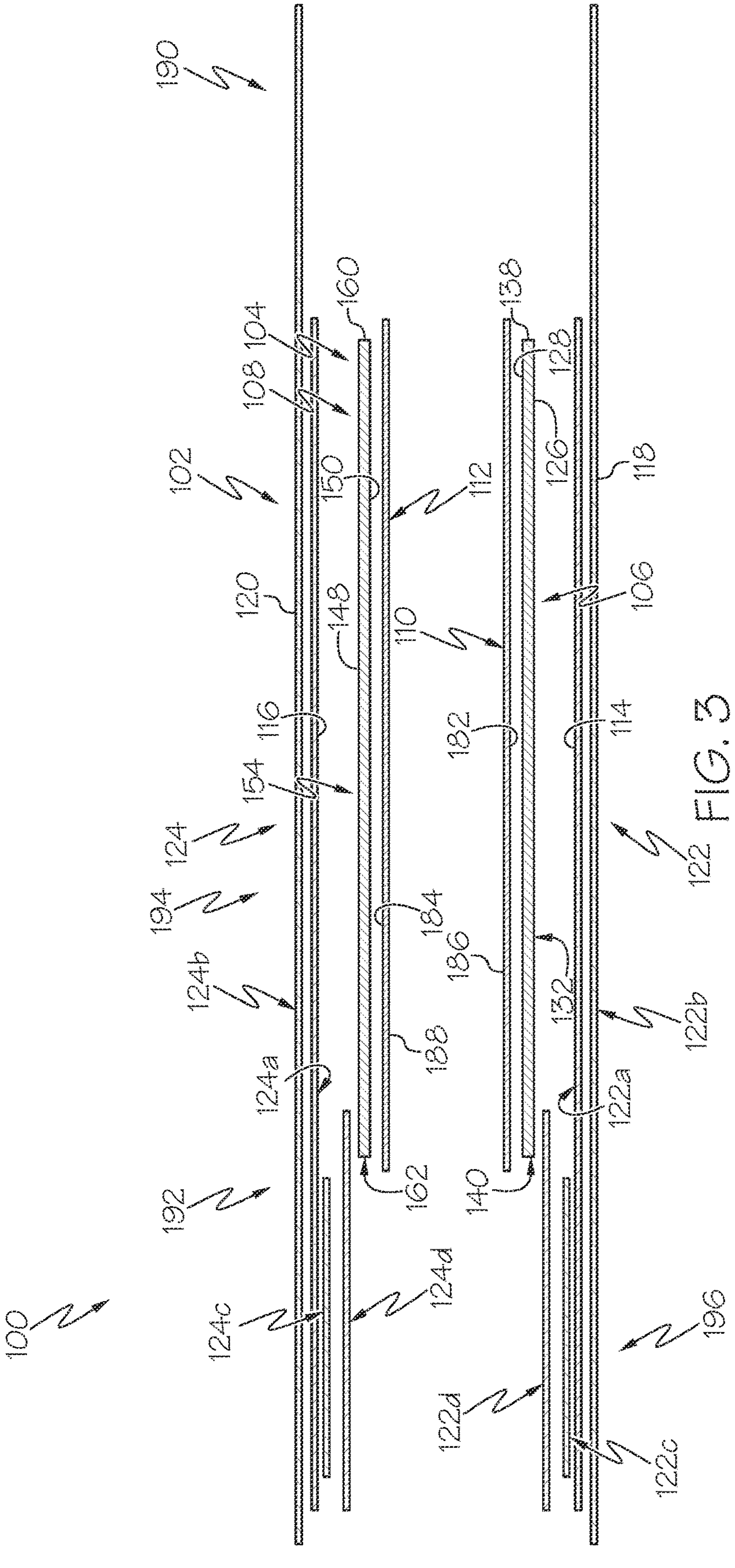
FIG. 3 schematically depicts an exploded, cross-sectional view of the artificial muscle of FIG. 1 taken along line 3-3 in FIG. 2, according to one or more embodiments shown and described herein.

In embodiments, as shown in FIG. 3, the first film layer 122 includes the first inner subfilm layer **122*a*, the first outer subfilm layer 122*b*, a first reinforcing layer 122*c*, and a first backing layer 122*d*. The first reinforcing layer 122*c* is provided between the first inner subfilm layer 122*a* and the first backing layer 122*d*. As shown, only a single first reinforcing layer 122*c* is provided. However, it should be appreciated that a plurality of first reinforcing layers 122*c* may be provided between the first inner subfilm layer 122*a* and the first backing layer 122*d*. The first reinforcing layer 122*c* may be in contact with and heat sealed between each of the first inner subfilm layer 122*a* and the first backing layer 122*d*. Accordingly, the first backing layer 122*d* is dimensioned to be greater than the first reinforcing layer 122*c* so that the first backing layer 122*d* may be heat sealed to the first inner subfilm layer 122*a* and enclose the first reinforcing layer 122*c* therebetween. Additionally, in embodiments, the first backing layer 122*d* comprises the same material as the first inner subfilm layer 122*a* and the first outer subfilm layer 122*b*. In embodiments, the first backing layer 122*d* partially overlaps the first electrode 106, specifically the bridge portion 140 of the first electrode 106. In embodiments, the first backing layer 122*d* also overlaps a portion of the first electrical insulator layer 110. The first reinforcing layer 122_c_ has an elasticity greater than an elasticity of the material forming each of the first inner subfilm layer 122_a_, the first outer subfilm layer 122_b_, and the first backing layer 122_d_. In embodiments, the first reinforcing layer 122_c_ includes a unidirectional laminate fabric material constructed from a sheet of ultra-high-molecular-weight polyethylene (UHMWPE) laminated between two sheets of polyester. In embodiments, the first reinforcing layer 122_c_ has a thickness of greater than or equal to 1 mil and less than or equal to 4 mil. In embodiments, the first reinforcing layer 122_c_ has a thickness of greater than or equal to 1 mil and less than or equal to 2 mil. In embodiments, the first reinforcing layer 122_c_ is a fabric material such as, for example, Dyneema®, Kevlar®, and the like. However, other suitable materials may be utilized for the first reinforcing layer 122**_c_.

Similarly, as shown in FIG. 3, the second film layer 124 includes the second inner subfilm layer 124_a_, the second outer subfilm layer 124_b_, a second reinforcing layer 124_c_, and a second backing layer 124_d_. The second reinforcing layer 124_c_ is provided between the second inner subfilm layer 124_a_ and the second backing layer 124_d_. As shown, only a single second reinforcing layer 124_c_ is provided. However, it should be appreciated that a plurality of second reinforcing layers 124_c_ may be provided between the second inner subfilm layer 124_a_ and the second backing layer 124_d_. The second reinforcing layer 124_c_ may be in contact with and heat sealed between each of the second inner subfilm layer 124_a_ and the second backing layer 124_d_. Accordingly, the second backing layer 124_d_ is dimensioned to be greater than the second reinforcing layer 124_c_ so that the second backing layer 124_d_ may be heat sealed to the second inner subfilm layer 124_a_ and enclose the second reinforcing layer 124_c_ therebetween. Additionally, in embodiments, the second backing layer 124_d_ comprises the same material as the second inner subfilm layer 124_a_ and the second outer subfilm layer 124_b_. In embodiments, the second backing layer 124_d_ partially overlaps the second electrode 108, specifically the bridge portion 162 of the second electrode 108. In embodiments, the second backing layer 124_d_ also overlaps a portion of the second electrical insulator layer 112. The second reinforcing layer 124_c_ has an elasticity greater than an elasticity of the material forming each of the second inner subfilm layer 124_a_, the second outer subfilm layer 124_b_, and the second backing layer 124_d_. In embodiments, the second reinforcing layer 124_c_ includes a unidirectional laminate fabric material constructed from a sheet of UHMWPE laminated between two sheets of polyester. In embodiments, the second reinforcing layer 124_c_ has a thickness of greater than or equal to 1 mil and less than or equal to 4 mil. In embodiments, the second reinforcing layer 124_c_ has a thickness of greater than or equal to 1 mil and less than or equal to 2 mil. In embodiments, the second reinforcing layer 124_c_ is a fabric material such as, for example, Dyneema®, Kevlar®, and the like. However, other suitable materials may be utilized for the second reinforcing layer 124_c_.

It should be appreciated that the first backing layer 122_d_ and the second backing layer 124_d_ are not scalable to one another such as, for example, by being heat sealed. As such, the expandable fluid region 196 (FIG. 4) is provided between the first backing layer 122_d_ and the second backing layer 124_d_. In addition, the film-facing surface 126 of the first electrode 106 is coupled or otherwise fixed to the second film layer 124 by any suitable methods such as, for example, heat-sealing or the like and, similarly, the film-facing surface 148 of the second electrode 108 is coupled or otherwise fixed to the second film layer 124 by any suitable methods such as, for example, heat-sealing or the like.

Due to the first reinforcing layer 122_c_ and the second reinforcing layer 124_c_ having an elasticity greater than an elasticity of the other layers of the housing 102 permanent deformation of the housing 102 of the artificial muscle 100 resulting from repeated use is prevented. Specifically, the BOPP forming the housing 102 is known to permanently distend or deform when subjected to forces greater than 15N. Accordingly, the first reinforcing layer 122_c_ and the second reinforcing layer 124_c_ reduce this permanent deformation.

Referring again to FIGS. 4 and 5, the electrode pair 104 is provided within the electrode region 194 of the unsealed portion 192 of the housing 102 and the artificial muscle 100 is actuatable between a non-actuated state (FIG. 4) and an actuated state (FIG. 5). It should be appreciated that the first film layer 122 and the second film layer 124 are generally depicted in FIGS. 4 and 5.

As shown in FIG. 4, in the non-actuated state, the first electrode 106 and the second electrode 108 are initially partially spaced apart from one another, at least at the first end 134, 156 of the tapered tab portions 132, 154. Due to the first film layer 122 being sealed to the second film layer 124 around the electrode pair 104, the second end 136, 158 of the tapered tab portions 132, 154 and the tapered walls 137, 139, 157, 159 are brought into contact with one another. Thus, dielectric fluid 198 is provided between the first electrode 106 and the second electrode 108, thereby separating the first end 134, 156 of the tapered tab portions 132, 154 proximate the expandable fluid region 196. Stated another way, when in the non-actuated state, a distance between the first end 134 of the tapered tab portion 132 of the first electrode 106 and the first end 156 of the tapered tab portion 154 of the second electrode 108 is greater than a distance between the second end 136 of the tapered tab portion 132 of the first electrode 106 and the second end 158 of the tapered tab portion 154 of the second electrode 108. This results in the electrode pair 104 zippering toward the expandable fluid region 196 when actuated. In the non-actuated state, the expandable fluid region 196 has a first height H1.

As shown in FIG. 5, in the actuated state, the first electrode 106 and the second electrode 108 are brought into contact with and oriented parallel to one another to force the dielectric fluid 198 into the expandable fluid region 196. This causes the dielectric fluid 198 to flow from the electrode region 194 between the first electrode 106 and the second electrode 108, and into the expandable fluid region 196 to inflate the expandable fluid region 196. Accordingly, when actuated, the first electrode 106 and the second electrode 108 zipper toward one another from the second ends 136, 158 of the tapered tab portions 132, 154 thereof, thereby pushing the dielectric fluid 198 into the expandable fluid region 196. The tapered walls 137, 139, 157, 159 facilitate the zippering from the second ends 136, 158. When in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

To move the first electrode 106 and the second electrode 108 toward one another, a voltage is applied by a power supply. In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 to deform in a first axial direction and causes the second film layer 124 to deform in an opposite second axial direction. Once the voltage being supplied to the first electrode 106 and the second electrode 108 is discontinued, the first electrode 106 and the second electrode 108 return to their initial, non-parallel position in the non-actuated state.

It should be appreciated that the present embodiments disclosed herein, specifically, the tapered tab portions 132, 154 with the interconnecting bridge portions 140, 162 (FIG. 1), provide a number of improvements over actuators, such as HASEL actuators, that do not include the tapered tab portions 132, 154. Embodiments of the artificial muscle 100 including a pair of tapered tab portions 132, 154 on each of the first electrode 106 and the second electrode 108, respectively, reduces the overall mass and thickness of the artificial muscle 100, reduces the amount of voltage required during actuation, and decreases the total volume of the artificial muscle 100 without reducing the amount of resulting force after actuation as compared to known HASEL actuators. More particularly, the tapered tab portions 132, 154 of the artificial muscle 100 provide zipping fronts that result in increased actuation power by providing localized and uniform hydraulic actuation of the artificial muscle 100 compared to known HASEL actuators. The bridge portions 140, 162 (FIG. 1) interconnecting the tapered tab portions 132, 154 also limit buckling of the tapered tab portions 132, 154 by maintaining the distance between adjacent tapered tab portions 132, 154 during actuation. Because the bridge portions 140, 162 are integrally formed with the tapered tab portions 132, 154, the bridge portions 140, 162 (FIG. 1) also prevent leakage between the tapered tab portions 132, 154 by eliminating attachment locations that provide an increased risk of rupturing.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196.

Figure 6:
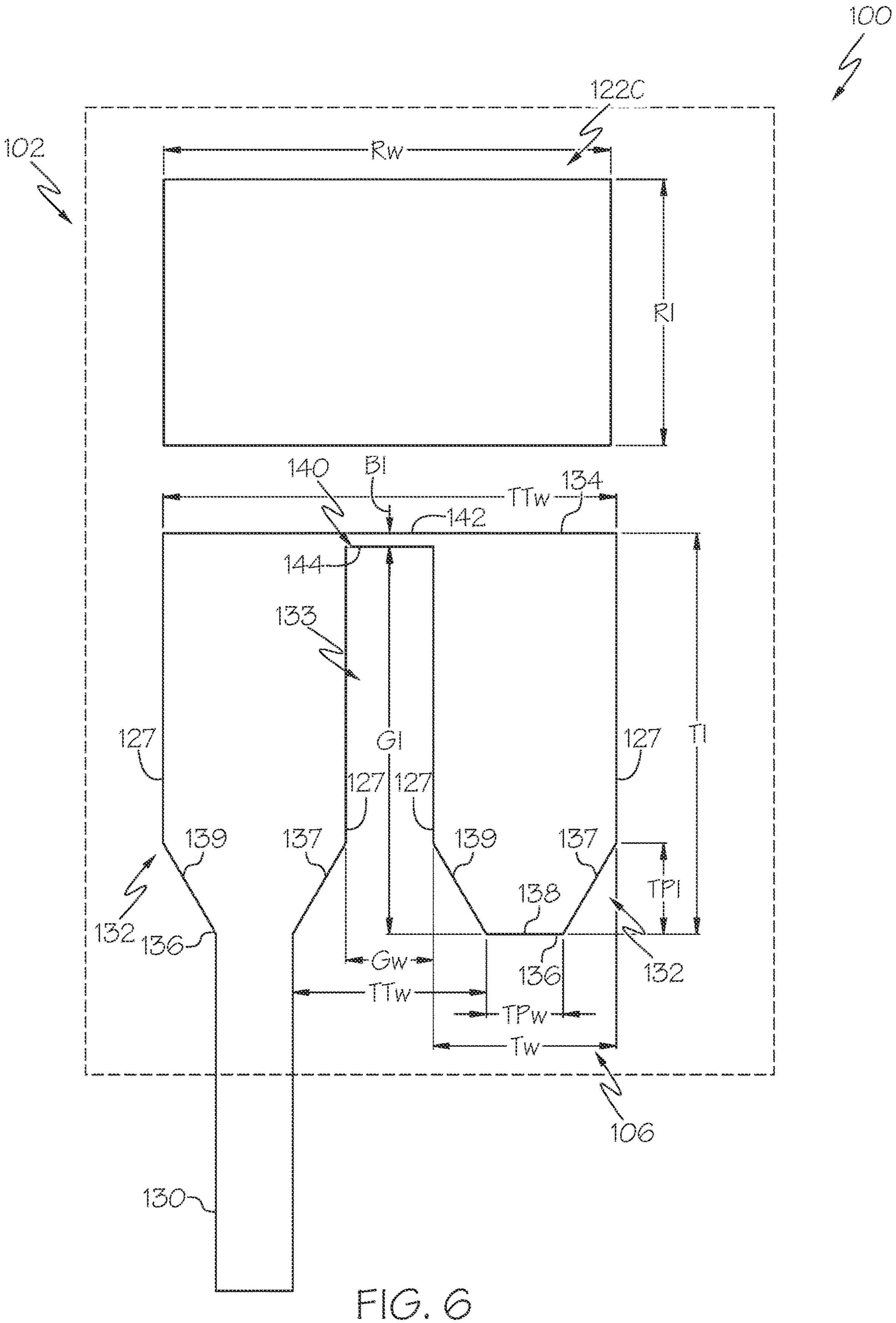
FIG. 6 depicts a top view of the artificial muscle of FIG. 1, according to one or more embodiments shown and described herein.

Referring now to FIG. 6, certain components of the artificial muscle 100 are illustrated including the first electrode 106 and the first reinforcing layer 122*c* within the housing 102. However, it should be appreciated that the first electrode 106 and the second electrode 108 have the same dimensions. Similarly, it should be appreciated that the first reinforcing layer 122*c* and the second reinforcing layer 124*c* have the same dimensions. Accordingly, only the dimensions of the first electrode 106 and the first reinforcing layer 122*c* are provided herein.

With respect to the first electrode 106, each tapered tab portion 132 of the first electrode 106 has a tab length Tl and the bridge portion 140 has a bridge length Bl. The tab length Tl is a distance from the first end 134 of the tapered tab portion 132 to the second end 136 of the tapered tab portion 132, and the bridge length Bl is a distance from the first end 142 of the bridge portion 140 to the second end 144 of the bridge portion 140. Accordingly, the tab length Tl of each tapered tab portion 132 is longer than the bridge length Bl of the bridge portion 140. Further, the tapered tab portion 132 includes a tapered wall length TPl. The tapered wall length TPl is the distance from a point between the first end 134 and the second end 136 of the tapered tap portion 132 where the distance between the tapered walls 137, 139 starts to decrease as they move towards the second end 136. In embodiments, the tapered wall length TPl may be between 1% and 50% of the tab length Tl. In other embodiments, the tapered wall length TPl may range between 5% and 15% of the tab length Tl.

In addition, each tapered tab portion 132 has a tab width Tw extending between opposite sides 127 of a respective tapered tab portion 132. A gap portion 133 is formed between the sides 127 of adjacent tapered tab portions 132 and adjacent the bridge portion 140. The gap portion 133 has a gap width Gw extending between opposite sides 127 of adjacent tapered tab portions 132 and a gap length Gl extending from the second end 144 of the bridge portion 140 and the second end 136 of the tapered tab portions 132. The first electrode 106 has a tapered tab width TTw extending across each of the pair of tapered tab portions 132 and the gap portion 133. Further, the tapered tab portion 132 includes a tapered portion width TPw. The tapered portion width TPw is the distance between the tapered walls 137, 139 where they meet the second end 138. In embodiments, the tapered portion width TPw may be between 10% and 90% of the tab width Tw. In other embodiments, the tapered portion width TPw may range between 25% and 75% of the tab length Tl.

In embodiments, the tapered tab portions 132 of the first electrode 104 define corners formed at substantially obtuse angles. However, in embodiments, these junctions or edges may be rounded. Accordingly, in embodiments, the first terminal 130 extends outward from the tapered walls 137, 139. Additionally, in embodiments, the bridge portion 140 extends between the tapered tab portions 132 to form corners partially defining the gap portion 133, the corners also being formed at substantially 90 degree angles such that the gap portion 133 is rectangular in shape between the tapered tab portions 132.

With respect to the first reinforcing layer 122*c*, the first reinforcing layer 122*c* has a reinforcing layer length Rl extending in a direction parallel to the tab length Tl. The first reinforcing layer 122*c* also has a reinforcing layer width Rw. In embodiments, the reinforcing layer width Rw is equal to the total tab width TTw of the first electrode 106.

In a first embodiment of the artificial muscle 100, the tab length Tl is greater than or equal to 3 cm and less than or equal to 4 cm. The tab width Tw is greater than or equal to 1 cm and less than or equal to 2 cm. The bridge length Bl is greater than or equal to 0.05 cm and less than or equal to 1 cm. The gap width Gw is greater than or equal to 0.5 cm and less than or equal to 1 cm. The gap length Gl is greater than or equal to 3 cm and less than or equal to 4 cm. The total tab width TTw is greater than or equal to 3 cm and less than or equal to 4.5 cm. The reinforcing layer length Rl of the first reinforcing layer 122*c* is greater than or equal to 2 cm and less than or equal to 3 cm.

In another embodiment of the artificial muscle 100, the tab length Tl is greater than or equal to 6 cm and less than or equal to 7 cm. The tab width Tw is greater than or equal to 2.5 cm and less than or equal to 4 cm. The bridge length Bl is greater than or equal to 0.1 cm and less than or equal to 1 cm. The gap width Gw is greater than or equal to 1 cm and less than or equal to 2 cm. The gap length Gl is greater than or equal to 6 cm and less than or equal to 7 cm. The total tab width TTw is greater than or equal to 7 cm and less than or equal to 8 cm. The reinforcing layer length Rl of the first reinforcing layer 122*c* is greater than or equal to 4 cm and less than or equal to 6 cm.

In yet another embodiment of the artificial muscle 100, the tab length Tl is greater than or equal to 12 cm and less than or equal to 13 cm. The tab width Tw is greater than or equal to 2.5 cm and less than or equal to 4 cm. The bridge length Bl is greater than or equal to 0.1 cm and less than or equal to 1 cm. The gap width Gw is greater than or equal to 1 cm and less than or equal to 2 cm. The gap length Gl is greater than or equal to 11 cm and less than or equal to 13 cm. The total tab width TTw is greater than or equal to 7 cm and less than or equal to 8 cm. The reinforcing layer length Rl of the first reinforcing layer 122*c* is greater than or equal to 4 cm and less than or equal to 6 cm.

It should be appreciated that the dimensions discussed herein are not limiting and other dimensions are contemplated as being within the scope of the present disclosure. For example, additional bridge lengths Bl are contemplated such as, for example, equal to or greater than 15 mm and less than or equal to 20 mm, equal to or greater than 10 mm and less than or equal to 15 mm, equal to or greater than 5 mm and less than or equal to 10 mm, and equal to or greater than 1 mm and less than or equal to 5 mm.

Referring now to FIG. 7, an actuation system 200 may be provided for operating an artificial muscle such as, for example, the artificial muscle 100, between the non-actuated state and the actuated state. The actuation system 200 may also be provided for operating the artificial muscles 100 or an artificial muscle assembly including a plurality of the artificial muscles 100 arranged in any suitable configuration such as, for example, in a stacked formation such that the expandable fluid region 196 of each artificial muscle 100 is axially positioned to overlap an adjacent expandable fluid region 196 of another artificial muscle 100. Thus, the actuation system 200 may include a controller 202, an operating device 204, a power supply 206, and a communication path 208. The various components of the actuation system 200 will now be described.

The controller 202 includes a processor 210 and a non-transitory electronic memory 212 to which various components are communicatively coupled. In some embodiments, the processor 210 and the non-transitory electronic memory 212 and/or the other components are included within a single device. In other embodiments, the processor 210 and the non-transitory electronic memory 212 and/or the other components may be distributed among multiple devices that are communicatively coupled. The controller 202 includes non-transitory electronic memory 212 that stores a set of machine-readable instructions. The processor 210 executes the machine-readable instructions stored in the non-transitory electronic memory 212. The non-transitory electronic memory 212 may comprise RAM, ROM, flash memories, hard drives, or any device capable of storing machine-readable instructions such that the machine-readable instructions can be accessed by the processor 210. Accordingly, the actuation system 200 described herein may be implemented in any conventional computer programming language, as pre-programmed hardware elements, or as a combination of hardware and software components. The non-transitory electronic memory 212 may be implemented as one memory module or a plurality of memory modules.

In some embodiments, the non-transitory electronic memory 212 includes instructions for executing the functions of the actuation system 200. The instructions may include instructions for operating the artificial muscle 100 based on a user command.

The processor 210 may be any device capable of executing machine-readable instructions. For example, the processor 210 may be an integrated circuit, a microchip, a computer, or any other computing device. The non-transitory electronic memory 212 and the processor 210 are coupled to the communication path 208 that provides signal interconnectivity between various components and/or modules of the actuation system 200. Accordingly, the communication path 208 may communicatively couple any number of processors with one another, and allow the modules coupled to the communication path 208 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 7, the communication path 208 communicatively couples the processor 210 and the non-transitory electronic memory 212 of the controller 202 with a plurality of other components of the actuation system 200. For example, the actuation system 200 depicted in FIG. 7 includes the processor 210 and the non-transitory electronic memory 212 communicatively coupled with the operating device 204 and the power supply 206.

The operating device 204 allows for a user to control operation of the artificial muscle 100. In some embodiments, the operating device 204 may be a switch, toggle, button, or any combination of controls to provide user operation. As a non-limiting example, a user may actuate the artificial muscle 100 into the actuated state by activating controls of the operating device 204 to a first position. While in the first position, the artificial muscle 100 will remain in the actuated state. The user may switch the artificial muscle 100 into the non-actuated state by operating the controls of the operating device 204 out of the first position and into a second position.

The operating device 204 is coupled to the communication path 208 such that the communication path 208 communicatively couples the operating device 204 to other modules of the actuation system 200. The operating device 204 may provide a user interface for receiving user instructions as to a specific operating configuration of the artificial muscle 100. In addition, user instructions may include instructions to operate the artificial muscle 100 only at certain conditions.

The power supply 206 (e.g., battery) provides power to the artificial muscle 100. In some embodiments, the power supply 206 is a rechargeable direct current power source. It is to be understood that the power supply 206 may be a single power supply or battery for providing power to the artificial muscle 100. A power adapter (not shown) may be provided and electrically coupled via a wiring harness or the like for providing power to the artificial muscle 100 via the power supply 206.

In some embodiments, the actuation system 200 also includes a display device 214. The display device 214 is coupled to the communication path 208 such that the communication path 208 communicatively couples the display device 214 to other modules of the actuation system 200. The display device 214 may output a notification in response to an actuation state of the artificial muscle 100 or indication of a change in the actuation state of the artificial muscle 100.

Moreover, the display device 214 may be a touchscreen that, in addition to providing optical information, detects the presence and location of a tactile input upon a surface of or adjacent to the display device 214. Accordingly, the display device 214 may include the operating device 204 and receive mechanical input directly upon the optical output provided by the display device 214.

In some embodiments, the actuation system 200 includes network interface hardware 216 for communicatively coupling the actuation system 200 to a portable device 218 via a network 220. The portable device 218 may include, without limitation, a smartphone, a tablet, a personal media player, or any other electric device that includes wireless communication functionality. It is to be appreciated that, when provided, the portable device 218 may serve to provide user commands to the controller 202, instead of the operating device 204. As such, a user may be able to control or set a program for controlling the artificial muscle 100 without utilizing the controls of the operating device 204. Thus, the artificial muscle 100 may be controlled remotely via the portable device 218 wirelessly communicating with the controller 202 via the network 220.

From the above, it is to be appreciated that defined herein is an artificial muscle for inflating or deforming a surface of an object by selectively actuating the artificial muscle to raise and lower a region thereof. This provides a low profile inflation member that may operate on demand.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An artificial muscle comprising:

a housing comprising an electrode region and an expandable fluid region;

an electrode pair positioned in the electrode region of the housing, the electrode pair comprising a first electrode and a second electrode, the first electrode and the second electrode each comprising a pair of tapered tab portions and a bridge portion interconnecting the pair of tapered tab portions to substantially form a U-shape, the pair of tapered tab portions extending parallel to one another to define a gap portion between the pair of tapered tab portions, the tapered tab portions each having a first end proximate to the expandable fluid region and an opposite second end proximate the electrode region, each of the second ends tapering in a direction opposite the expandable fluid region; and a dielectric fluid housed within the housing, wherein the electrode pair is actuatable between a non-actuated state and an actuated state such that actuation from the non-actuated state to the actuated state directs the dielectric fluid into the expandable fluid region.

2. The artificial muscle of claim 1, wherein the housing comprises a first film layer and a second film layer partially sealed to one another to define a sealed portion of the housing, the housing further defining an unsealed portion surrounded by the sealed portion, wherein the electrode region and the expandable fluid region of the housing are disposed in the unsealed portion.

3. The artificial muscle of claim 2, wherein the first film layer and the second film layer each comprise one or more biaxially oriented polypropylene films.

4. The artificial muscle of claim 1, further comprising a first electrical insulator layer vacuum heat sealed to an inner surface of the first electrode and a second electrical insulator layer vacuum heat sealed to an inner surface of the second electrode.

5. The artificial muscle of claim 1, wherein the first electrode and the second electrode are each an aluminum-coated polyester electrode.

6. The artificial muscle of claim 1, wherein:

when the electrode pair is in the non-actuated state, the first electrode and the second electrode are non-parallel to one another, and when the electrode pair is in the actuated state, the first electrode and the second electrode are parallel to one another, such that the first electrode and the second electrode are configured to zipper toward one another when actuated from the non-actuated state to the actuated state.

7. The artificial muscle of claim 1, wherein the housing comprises a first reinforcing layer and a second reinforcing layer positioned substantially within the expandable fluid region, the first reinforcing layer at least partially overlaps the bridge portion of the first electrode, and the second reinforcing layer at least partially overlaps the bridge portion of the second electrode.

8. The artificial muscle of claim 1, wherein the first electrode and the second electrode are equal in dimension.

9. A method for actuating an artificial muscle assembly, the method comprising:

generating a voltage using a power supply electrically coupled to an electrode pair of an artificial muscle, the artificial muscle comprising a housing with an electrode region and an expandable fluid region, wherein:

the electrode pair is positioned in the electrode region of the housing;

the electrode pair comprises a first electrode and a second electrode, the first electrode and the second electrode each comprise a pair of tapered tab portions and a bridge portion interconnecting the pair of tapered tab portions to substantially form a U-shape, the tapered tab portions each having a first end proximate to the expandable fluid region and an opposite second end proximate the electrode region, each of the second ends tapering in a direction opposite the expandable fluid region, the pair of tapered tab portions extending parallel to one another to define a gap portion between the pair of tapered tab portions, and a dielectric fluid is housed within the housing; and applying the voltage to the electrode pair of the artificial muscle, thereby actuating the electrode pair from a non-actuated state and an actuated state such that the dielectric fluid is directed into the expandable fluid region of the housing and expands the expandable fluid region.

10. The method of claim 9, further comprising:

partially heat sealing a first film layer of the housing to a second film layer of the housing to define a sealed portion and an unsealed portion surrounded by the sealed portion, wherein the electrode region and the expandable fluid region of the housing are disposed in the unsealed portion.

11. The method of claim 10, wherein the first film layer and the second film layer each comprise one or more biaxially oriented polypropylene films.

12. The method of claim 9, further comprising:

communicatively coupling a controller to the electrode pair, and operating the controller to direct a voltage from the power supply across the first electrode and the second electrode to actuate the artificial muscle from the non-actuated state to the actuated state.

13. The method of claim 9, wherein the housing comprises a first reinforcing layer and a second reinforcing layer positioned substantially within the expandable fluid region, the first reinforcing layer at least partially overlapping the bridge portion of the first electrode, and the second reinforcing layer at least partially overlapping the bridge portion of the second electrode.

14. The method of claim 9, wherein the first electrode and the second electrode are equal in dimension.

* * * * *